United States Patent [19]

Simpson et al.

[11] Patent Number: 5,441,510

[45] Date of Patent: Aug. 15, 1995

[54] BI-AXIAL CUTTER APPARATUS FOR CATHETER

[75] Inventors: John B. Simpson, Woodside; Scott C. Anderson, Mountain View; John J. Frantzen, Copperopolis; Peter S. Brown, Mountain View; James M. Cannon, Jr., Santa Clara; Geoffrey A. Orth, San Jose, all of Calif.

[73] Assignee: Technology Development Center, Redwood City, Calif.

[21] Appl. No.: 250,319

[22] Filed: May 27, 1994

Related U.S. Application Data

[63] Continuation of Ser. No. 115,206, Sep. 1, 1993, abandoned.

[51] Int. Cl.⁶ .............................................. A61B 17/32
[52] U.S. Cl. ..................................... 606/159; 606/170; 606/180; 604/22
[58] Field of Search ............... 606/159, 170, 171, 180; 604/22

[56] References Cited

U.S. PATENT DOCUMENTS

| | | |
|---|---|---|
| Re. 33,569 | 4/1991 | Gifford, III et al. . |
| 4,669,469 | 6/1987 | Gifford, III et al. ............... 606/159 |
| 4,781,186 | 11/1988 | Simpson et al. . |
| 4,794,931 | 1/1989 | Yock . |
| 4,979,951 | 12/1990 | Simpson . |
| 5,000,185 | 3/1991 | Yock . |
| 5,007,917 | 4/1991 | Evans ............... 606/170 |
| 5,071,425 | 12/1991 | Gifford, III et al. . |
| 5,078,722 | 1/1992 | Stevens . |
| 5,084,010 | 1/1992 | Plaia et al. . |
| 5,085,662 | 2/1992 | Willard ............... 606/159 |
| 5,087,265 | 2/1992 | Summers . |
| 5,092,873 | 3/1992 | Simpson et al. . |
| 5,100,424 | 2/1992 | Jang et al. . |
| 5,135,531 | 8/1992 | Shiber . |
| 5,156,610 | 10/1992 | Reger . |
| 5,158,564 | 10/1992 | Schnepp et al. . |
| 5,226,909 | 7/1993 | Evans et al. . |
| 5,250,059 | 10/1993 | Andreas et al. . |

*Primary Examiner*—Stephen C. Pellegrino
*Assistant Examiner*—William Lewis
*Attorney, Agent, or Firm*—Douglas A. Chaikin

[57] ABSTRACT

An cutter apparatus for removing obstructive tissue has a distal housing having a window for invaginating tissue. An axially reciprocating and rotating cutting blade makes successive longitudinal cuts while slowly rotating across the open window. An axial guide assembly holds the cutting edge of the blade in a cutting path immediately adjacent to the inner surface of the housing. The shape and motion of the cutting blade pares off a generally uniformly thick slice of tissue from the stenosis and directs it toward the interior of the housing. A spiral parting edge opposed to the rotating cutting edge provides clean separation of the tissue slice from the stenosis. The tissue slice is received in a chamber internal to the housing and is retained by the blade and guide assembly for later removal from the patient.

12 Claims, 6 Drawing Sheets

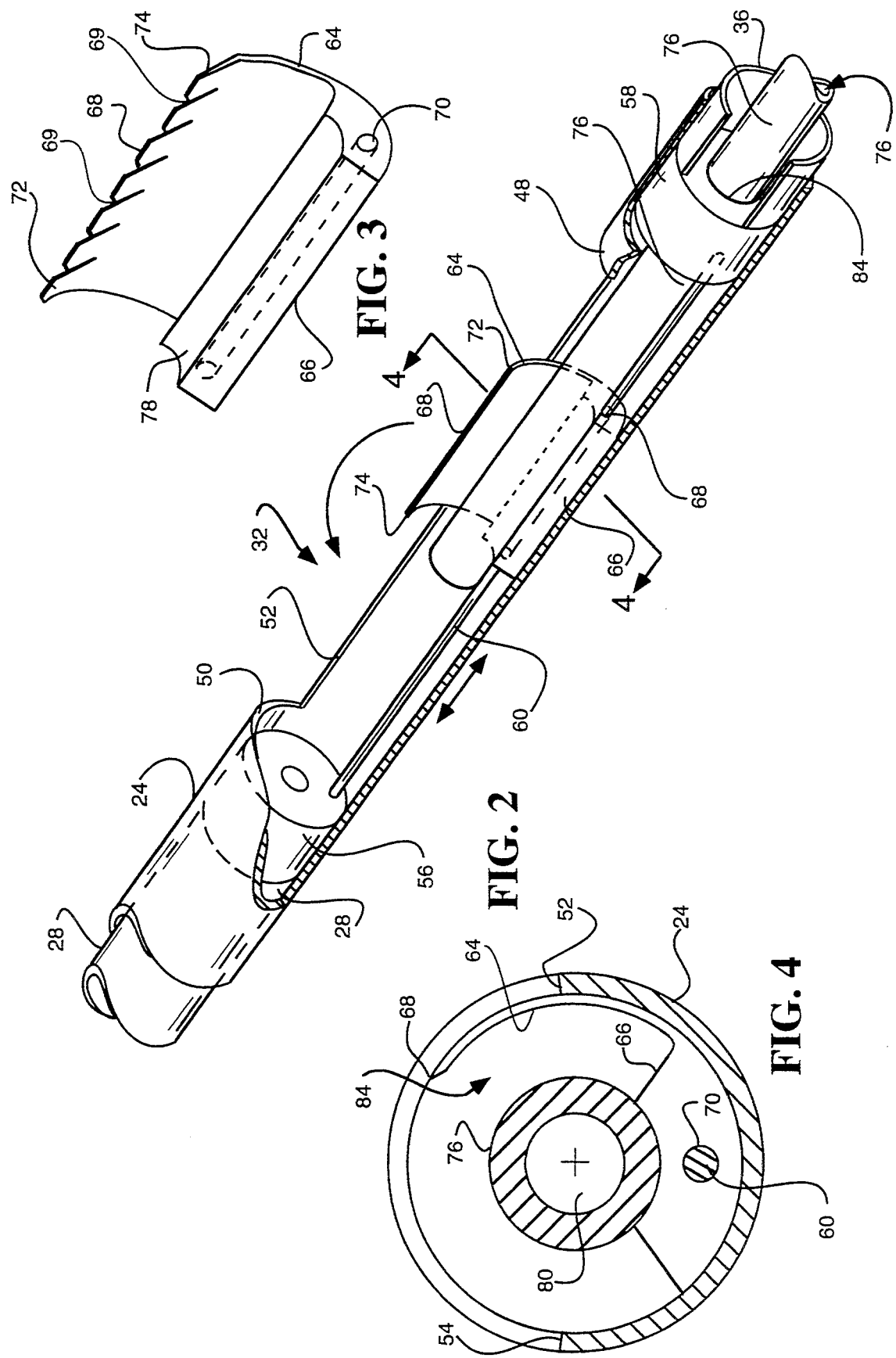

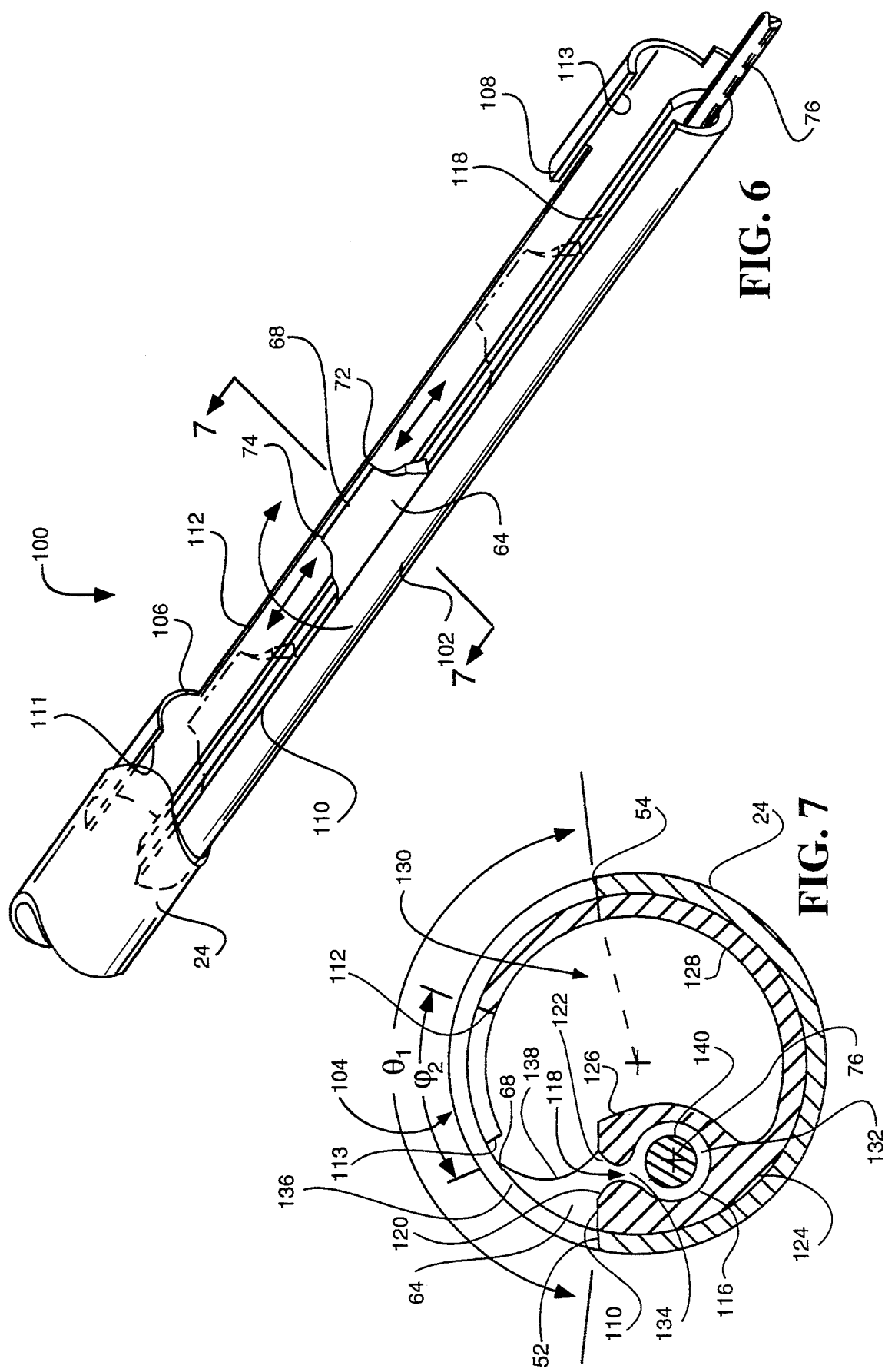

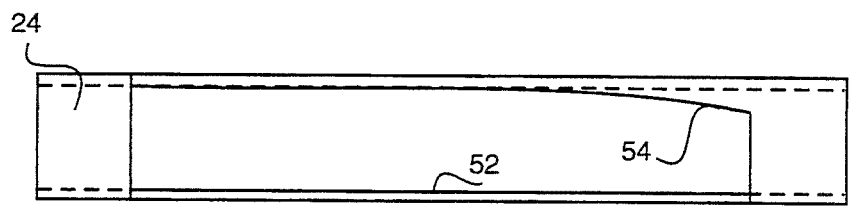
FIG.9
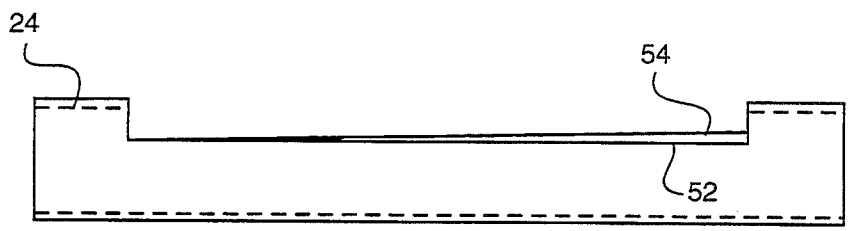
FIG.10
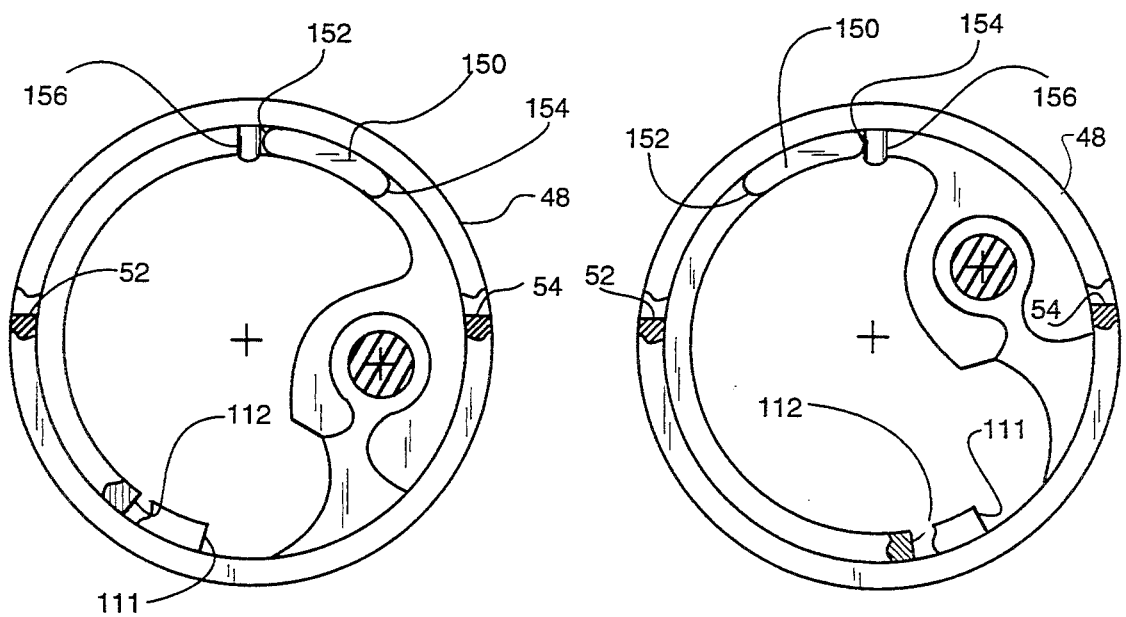
FIG. 11  FIG.12

BI-AXIAL CUTTER APPARATUS FOR CATHETER

This is a continuation of application Ser. No. 08/115,206 filed on Sep. 1, 1993 now abandoned.

BACKGROUND OF THE INVENTION

1. Field of the Invention

The present invention relates generally to atherectomy catheters and more particularly to a catheter having a cutting apparatus for cutting along two different axis.

2. Previous Art

The high incidence of disease and death from atherosclerosis in the general population has stimulated intense interest in devices and procedures for treatment. Atherosclerosis is a disease of the circulatory system caused by excess internal tissue growth or fatty or calcified deposits within blood vessels in the human. These deposits are generally characterized as stenoses. Stenoses tend to reduce the cross sectional area of the blood vessels which results in reduced blood circulation. Severe cases of blockage can cause or contribute to myocardial infarction, stroke and other conditions.

Procedures have been developed for treatment of these conditions, such as coronary bypass surgery. The expense and risk of bypass surgery has stimulated the use of alternative treatments such as balloon angioplasty, wherein a balloon catheter is positioned within a blood vessel adjacent to a blockage and inflated to compress or displace the blockage. The expense and risk of balloon angioplasty is substantially less than for bypass surgery but may be ineffective if the blockage is asymmetrical, highly calcified or composed of highly fibrous tissue. There is also some risk of restenoses since the stenotic material, which remains in place in the vessel, can grow back.

Atherectomy devices for clearing or opening blood vessels obstructed by stenotic material have been developed to counter these disadvantages and are well known. In an atherectomy procedure, the stenotic material causing the obstruction in the vessel is cut or otherwise separated from the interior of the vessel and removed.

A number of atherectomy devices have been disclosed. An example of such a device is U.S. Pat. No. 4,020,847 to Clark which discloses a blunt hollow tube on the end of a flexible catheter. A cutting edge on side of a lengthwise window opening in the tube is used to cut stenoses from a vessel by rotating the tube in a cutting direction defined by the cutting edge. Stenotic tissue intruding or invaginated into the opening is subjected to a cutting action tending to pull the tissue in the direction of rotation and separate it from the tissue outside the tube. A disadvantage of this structure is the tendency of the separated edge to be rough due to the distortion induced in the tissue as it reacts to the pulling action of the rotation of the tube and cutting edge. Also, the angular extent of the window opening limits the amount of tissue invaginated into the housing thereby limiting the depth of cut. A small opening requires multiple cuts to achieve a desired depth of cut. A large opening increases the distortion of the tissue and roughness of the cut. The shape of the cut tends to be non-uniform due to the tissue distortion caused by the cutting force directed normal to the cutting window edge.

Another example of an atherectomy device having a rotary cutter is shown in U.S. Pat. No. 4,986,807 to Farr. This discloses a blade having a rotating cutting edge capable of projecting beyond the diameter of the housing containing the blade. This allows the device to make a cutting area larger than that possible without such projection. The uni-rotational rotary cutting action of the blade tends to distort the tissue as it cuts leaving a scalloped cut of non-uniform thickness. In addition, there is some risk of perforation of the blood vessel wall since the cutting edge does project beyond the housing wall.

An example of an atherectomy device having combined rotary and axial cutting motion is disclosed in U.S. Pat. No. 5,156,610 to Reger. Several blades are mounted in a helical basket configuration and spaced angularly apart from one another about the associated ends of two concentric sheaths in such a way that longitudinal and rotary relative movement of the sheaths selectively bows the blades arcuately outward into a cutting position or draws the blades flat into alignment with the sheaths. The degree of bowing determines the diameter of the cutting action.

Removal of cutaway pieces of the stenoses is accomplished by either pull-back of a balloon embolectomy catheter or by use of a latex membrane enshrouding the blades and used to trap the tissue shavings within the membrane. The diameter of the cut is not limited by a housing surrounding the cutting blades thus increasing the possible risk of vessel perforation if cutting is too aggressive. The mechanism is a complicated and delicate assembly.

Another example of an atherectomy catheter having a rotatable and axial translatable cutter is disclosed in U.S. Pat. No. 5,154,724 to Andrews. An expandable cutter head having spaced apart blades radially extending from a cutter sleeve at the distal end of the cutter head is axially extended from a guiding catheter inside a blood vessel. A torque tube and expander cable within the catheter control the radius of the cutter head blade expansion. The outermost radius of the blades at the cutter head determine the depth of tissue cut from the vessel wall.

A vacuum applied to the proximal end of the torque tube is used to draw off the material cut away by the cutter. The effectiveness of the vacuum for removing material is limited by the small diameter of the lumen required for small blood vessels and the long path along the catheter.

It is difficult to properly direct and stabilize such a cutter. The depth of the tissue cut from the vessel wall is dependent on the skill and aggressiveness of the operator. There is no safeguard provided to limit the cutting depth as the blades are extended, hence cutting must be limited to a passageway well removed from the vessel wall. Such an approach would not be effective for hard deposits, as it would be difficult to provide sufficient force to cause the blades to press in a radial direction.

The control problem is addressed by a second approach. In this approach the catheter has a cutter window disposed along the side of the catheter. A balloon is used to stabilize the catheter and to mechanically force the window against the deposits, causing some of the deposits to enter the housing itself. A rotating circular cutting blade is advanced longitudinally parallel to the catheter axis, thereby cutting deposits which extend through the window into the housing. The extension of material in this manner is termed invagination. An example of an atherectomy catheter illustrating this approach is in U.S. Pat. No. 4,979,951 to Simpson. This discloses a housing containing a rotating cup-like cutter which moves past a window opening in the housing. Tissue invaginated in the opening is cut by the axial motion of the cutter.

This approach has certain limitations. First, the depth of such a cut and the amount of material removed is limited by the angular width of the window. The width of the window is limited to that required to safely hold the cutter in the housing. The diameter is limited to the sheath size selected for a given artery.

Secondly, The cut is not uniform along the axial direction. The cutting force is directed primarily to the bulk of the invaginated tissue. When the cutter first encounters the invaginated tissue, it cuts and engages the material. As the cutter is advanced, it pulls on the material, drawing more through the cutter window. This ususally causes a distortion of tissue as the cut begins thin and thickens as it proceeds to the terminal end of the cut. This can result in a steep slope at the back end of the cut as the cutter passes the end of the window. The resulting teardrop-shape of the axial cross-section leaves a nonuniform depth along the extent of the cut.

Thirdly, the limited angular width of the window opening which prevents the cutter from leaving the housing, also tends to cause a scalloped cut in the circumferential direction. Scalloped cuts tend to cause the housing to orient preferentially into the trough created by the scallop. This makes it more difficult to extend the tissue removal in a smooth angular manner by doing multiple cuts closely juxtaposed.

For each of the devices disclosed in these references, the cutting direction is primarily at right angles to the cutting edge. Consequently, the tissue being cut experiences a force tending to distort the tissue shape so that the cutting depth is nonuniform along the extent of the cut. Steep edges at the separation point tend to cause the cutter housing to preferentially locate in the previous cut such that repetitive cuts increase thickness nonuniformity.

Accordingly, there is a need for an atherectomy device which provides for a defined tissue cut with a generally uniform depth across the extent of the cut. Also the cut needs to have a relatively shallow incline with a well defined edge at the separation of the cut stenotic tissue from the remaining tissue to prevent the housing from preferentially locating in a previous cut.

In addition, there is a need for receiving the cut tissue and preventing it from being reintroduced into the blood vessel.

SUMMARY OF THE INVENTION

It is an object of this invention to provide an atherectomy cutting apparatus for removing stenotic tissue in slices having uniform thickness cross sections over a wide extent.

It is a further object of this invention to provide an atherectomy cutting apparatus having improved control over the depth of thickness of slices removed from stenotic tissue.

It is yet a further objective of this invention to provide an atherectomy cutting apparatus which receives and contains the cut tissue for removal from the patient.

In accordance with the above objects and those that will be mentioned and will be apparent below, the atherectomy cutter apparatus for use with a catheter within a biological conduit in accordance with this invention comprises:

a tubular member defining a housing, the housing having a window for intimate contact with tissue in the biological conduit, the window including a distal edge and a proximal edge and having an edge between the distal and proximal edges having at least one contiguous submultiple edge defining a parting edge, each submultiple edge including at least one spiral increment; and a cutter assembly including:
cutting means for cutting tissue within the biological conduit,
means for rotating the cutting means within the housing, and
means for translating the cutting means within the housing,
whereby the cutting means is adapted to remove a slice of tissue from within the biological conduit by rotating and translating the cutting means.

In certain preferred embodiments, the housing window includes a parting edge. In one particular embodiment having a parting edge, the housing window comprises:

a distal edge and a proximal edge a parting edge between the distal edge and proximal edge, the parting edge being comprised of one or more contiguous submultiple edges of the length of the parting edge, each submultiple edge comprising a succession of one or more spiral cutting increments, the succession of spiral cutting increments forming a continuous line along each respective submultiple edge, beginning at one end of each submultiple edge, the spiral cutting increments of each submultiple edge terminating at the opposite end of each submultple edge, the spiral cutting increments of each submultiple edge being smoothly and continuously displaced in a circumferential direction defined by the rotation of the cutter means, each spiral increment of each submultiple edge having a cutting edge lying adjacent to the inner surface of the outer housing; and the cutter means including a blade cutting edge lying immediately adjacent to the inner surface of the outer housing, the blade cutting edge defining a cutting direction facing in the direction of the parting edge and facing in the rotational cutting direction;

whereby the parting edge and the blade cutting edge cooperate for removing the slice of tissue from the biological conduit tissue by separating the slice from the conduit tissue by rotating and translating the blade cutting edge past the parting edge in the rotational cutting direction.

In a preferred embodiment the biaxial cutting apparatus includes the means for rotating the cutter means includes a rotational limit means for limiting the extent of a rotational cutting stroke of the cutter means to a preselected portion of one complete rotation, the means for limiting rotation having a first limit defining the beginning of a rotational cutting stroke wherein the cutter means is positioned prior to cutting tissue in contact with the housing window, the means for limiting rotation further having a second limit defining the end of the rotational cutting stroke wherein the cutter means is positioned after completing a cutting stroke past the housing window.

In another preferred embodiment, the cutting means includes a translational limit means for limiting the longitudinal extent of an axial cutting stroke of the cutting means to a preselected multiple of the longitudinal extent of the catheter housing window.

In general, a housing having a window is placed in desired relationship to the stenotic tissue. A control unit drives a cutter apparatus in a repetitive axially reciprocal motion sequentially back and forth past a proximal window edge and a distal window edge. Simultaneously, the control unit rotates the cutting apparatus relatively slowly from one longitudinal edge past the opposite longitudinal part-off edge.

This repetitive axial movement of a cutting edge combined with the successive slow, smooth rotary movement provides a highly controlled cutting motion which does not greatly disturb the bulk of the invaginated tissue during the cutting process. Since the cutting force is tangentially applied to a relatively small segment of the bulk of invaginated tissue with each longitudinal pass, the distortion of the shape of the balance of the tissue is small. This results in a microtome-like cutting process which takes relatively small successive cuts to give a precise cut tissue slice.

The combined axial translation and rotational movement of the cutting blade removes a tissue slice with each successive axial excursion. The tissue slice curls inward to the housing until the blade cutting edge approaches the opposite part-off edge. In one preferred embodiment, the shape of the part-off edge is such that successive axial passes of the blade separate small increments of the final connection of the tissue from the stenosis. The last pass of the blade cutting edge next to the part-off edge removes the last connection of the tissue slice with the stenosis. At this point the tissue slice is separated from the stenosis and is received into a chamber for capture and disposal.

It is an advantage of this invention to provide a cutting means for cutting uniform thickness slices from stenoses.

It is a further advantage of this invention to provide a means for cutting tissue slices of desired thickness from stenoses.

It is yet another advantage of this invention to provide a cutting means for cutting wide slices of tissue from stenoses.

BRIEF DESCRIPTION OF THE DRAWING

For a further understanding of the objects and advantages of the present invention, reference should be had to the following detailed description, taken in conjunction with the accompanying drawing, in which like parts are given like reference numerals and wherein:

FIG. 2 is a perspective view of a portion of the biaxial cutting apparatus of FIG. 1, illustrating the housing.

FIG. 3 is a perspective view of an alternate longitudinal cutting blade.

FIG. 4 is a cross sectional view taken along line 4—4 of FIG. 2 looking in the direction of the arrows.

FIG. 6 is a perspective view of the housing and axial guide of a preferred embodiment of the bi-axial cutting atherectomy apparatus in accordance with this invention.

FIG. 7 is a cross-sectional view of the housing of FIG. 6 taken along line 7—7 and looking in the direction of the arrows.

FIGS. 9 and 10 illustrate the parting edge 54 of the housing of FIG. 2 and FIG. 8.

FIG. 11 is a cross sectional view of the embodiment of FIG. 6 looking from the proximal end with the cutter in a starting position.

FIG. 12 is a cross sectional view of the embodiment of FIG. 6 looking from the proximal end with the cutter in a stopping position.

DETAILED DESCRIPTION OF THE INVENTION

Figure 1:
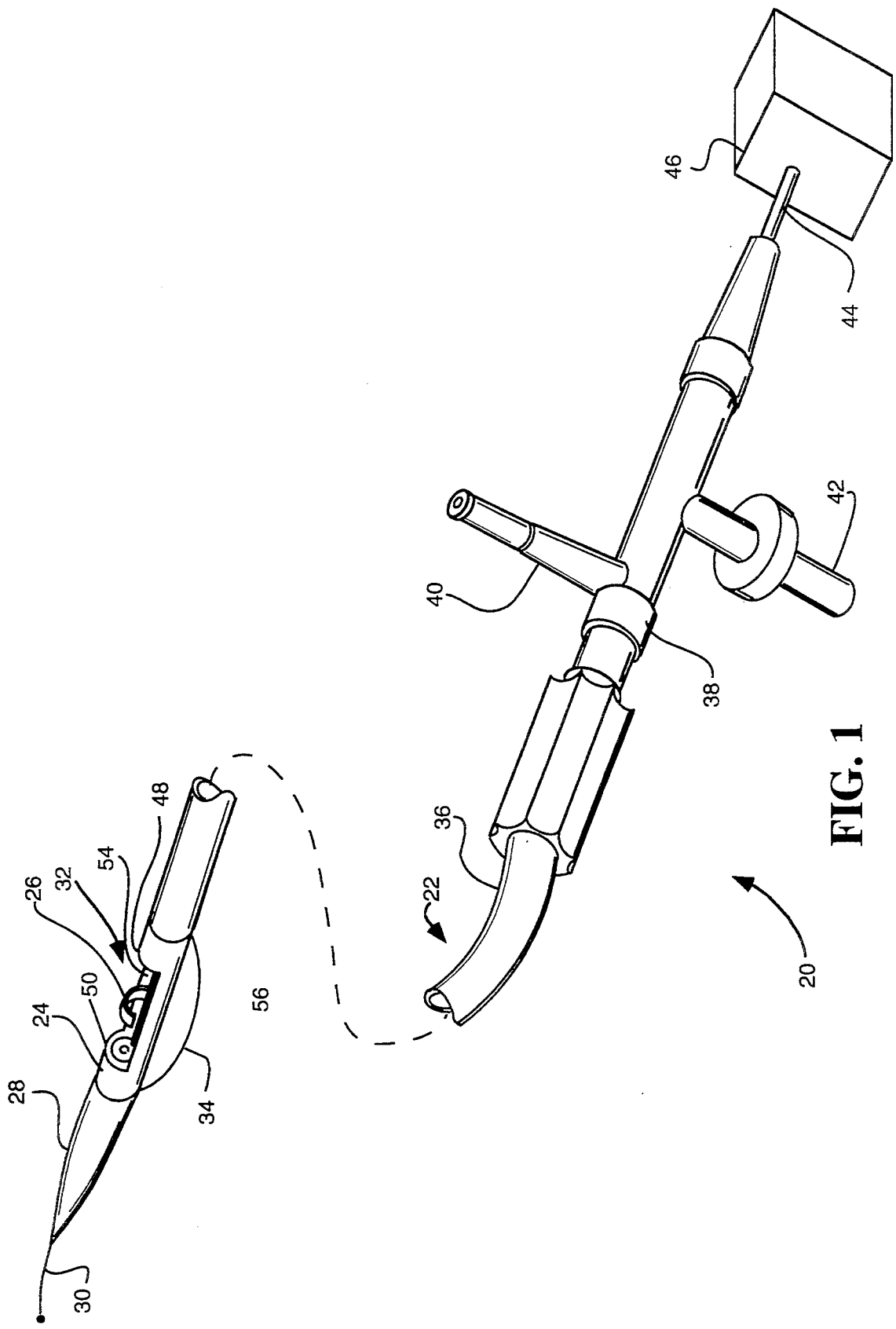
FIG. 1 is a perspective view of the biaxial cutting atherectomy apparatus in accordance with this invention.

The invention will now be described with respect to FIG. 1, which illustrates the biaxial cutter atherectomy apparatus in accordance with this invention generally denoted by the numeral 20. The apparatus includes a catheter assembly 22 having a housing 24 for housing a biaxial cutter apparatus 26. The housing 24 is fitted at its distal end with a nosecone 28 from which one end a guidewire 30 extends distally. A window 32 disposed along one side of the housing 24 provides access for invaginating stenotic tissue from the walls of a biological vessel into the interior of the housing 24.

The cutter 20 is provided with a structure for urging the housing 24 towards the stenotic material. The preferred embodiment includes such a structure, namely a balloon 34. The balloon 34 is disposed along one side of the housing 24 opposite the window 32. The balloon 34 is inflated to urge the window 32 against the tissue which is to be removed. The catheter assembly 22 is extended at its proximal end as a flexible assembly 36 for attachment to the proximal port assembly 38.

It will be appreciated that other such structures are also within the spirit and scope of the invention. Such structures may include wire or other mechanical devices for urging the housing 24 towards the stenotic material.

There are two infusion ports 40 and 42 located on the proximal port assembly 38. The ports 40 and 42 permit transfer of fluids between the external environment (not shown) and the catheter assembly 22. The port 42 provides access for introduction of saline flushing fluid. The port 40 provides access for inflating and deflating the balloon 34.

A flexible drive member (not shown) having a proximal and a distal end, is disposed in the catheter 36. The drive member distal end is connected to the biaxial cutter apparatus 26. The drive member proximal end passes rotatably through the flexible assembly 36, the port assembly 38 and is connected to a connection means 44. The connection means 44 connects to a biaxial cutter control unit 46.

The biaxial cutter control unit 46, provides rotary and reciprocal motion for the flexible drive members connected to the cutter apparatus 26 by manual or motor operation.

The invention will now be described with respect to FIGS. 2-5. With particular respect to FIG. 2, there is shown a portion of the housing 24.

The cylindrical housing 24 has a central axis and a distal and proximal end. The housing 24 is formed of a suitable rigid tubular material such as stainless steel. The housing 24 has a longitudinal window 32 disposed on one side. The window 32 is defined by circumferential-sector-shaped distal and proximal edges 50, 48, respectively. The distal edge 50 and the proximal edge 48 are connected by longitudinal edges 52 and 54. The window 32 is provided to allow invagination of stenotic tissue within the housing 24.

The window 32 has an opening having an angle with respect to the central axis of the housing 24 of more than 100 degrees and less than 270 degrees. The length of the opening 32 is defined by the distance between distal edge 50 and proximal edge 48. This distance is more than 0.2 inches and less than one inch.

The region between the window edge 52 and the window edge 54 provides an opening for receiving stenotic tissue to be cut. The width of the opening 32 controls the amount of tissue which can be received. A narrow opening will admit less tissue than a wide opening. The window edge 52 is the first edge where cutting will occur. the window edge 54 is the last point where cutting will occur. The window edge 54 defines a parting edge where a tissue slice is removed from the stenoses.

The parting edge 54 provides a cutting edge for removing a tissue slice cut from the stenotic tissue. The parting edge 54 is configured in the shape of a suitably shallow spiral lying in the cylindrical surface defined by the inner circumference of the housing 24. The spiral edge 54 extends between the distal edge 50 and the proximal edge 48. Parting edge 54 is discussed in greater detail below.

Within the housing 24 there is included a closely fitting but rotatably free cylindrical distal bearing 56 and a proximal bearing 58. The proximal end of bearing 56 is located distal to the distal window edge 50. The distal end of bearing 58 is located proximal to the proximal window edge 48. The bearings 56 and 58 are made from a suitable low friction material such as stainless steel.

The distal bearing 56 is prevented from moving further toward the distal end by the proximal end of the tubular nose cone 28. The nose cone 28 is sized to fit closely within housing 24. The nose cone 28 is fixed in place by a suitable method such as gluing with an epoxy or the like. The proximal end of the nose cone 28 is made of a material such as stainless steel to provide a suitably smooth surface for the distal surface of the bearing 56.

The proximal bearing 58 is similarly prevented from moving further to the proximal and of the housing 24 by the distal end of the catheter assembly 36 which is provided with a slidably smooth bearing surface for the proximal surface of bearing 58. The distal end of catheter assembly 36 fits closely within the housing 24. The distal end of catheter assembly 36 is similarly fixed in place within the proximal end of housing 24 by a means such a gluing with a suitable medical grade epoxy.

The proximal surface of distal bearing 56 is provided with a hole 63. The hole 63 receives the distal end of a suitably stiff guide beam 60. The distal end of beam 60 is glued in place with a suitable medical grade epoxy. The distal surface of proximal bearing 58 is similarly provided with a hole 62. The hole 62 receives the proximal end of guide beam 60. The proximal end of beam 60 is similarly fixed in place.

An arcuate cutter blade 64 projects circularly from a base 66. The circular projection of blade 64 from the base 66 defines a cutting direction. The circular projection of blade 64 is terminated by a sharpened blade edge 68.

With respect to FIG. 3, there is shown an alternate blade 64. The alternate blade 64 has the blade edge 68 divided into two or more blade regions separated by blade slots 69.

Cutting of tissue invaginated into window 32 is done by the blade edge 68 as it moves rotationally and axially past the window edge 52. Tissue cutting by blade edge 68 alone continues until blade edge 68 approaches spiral edge 54.

Figure 5:
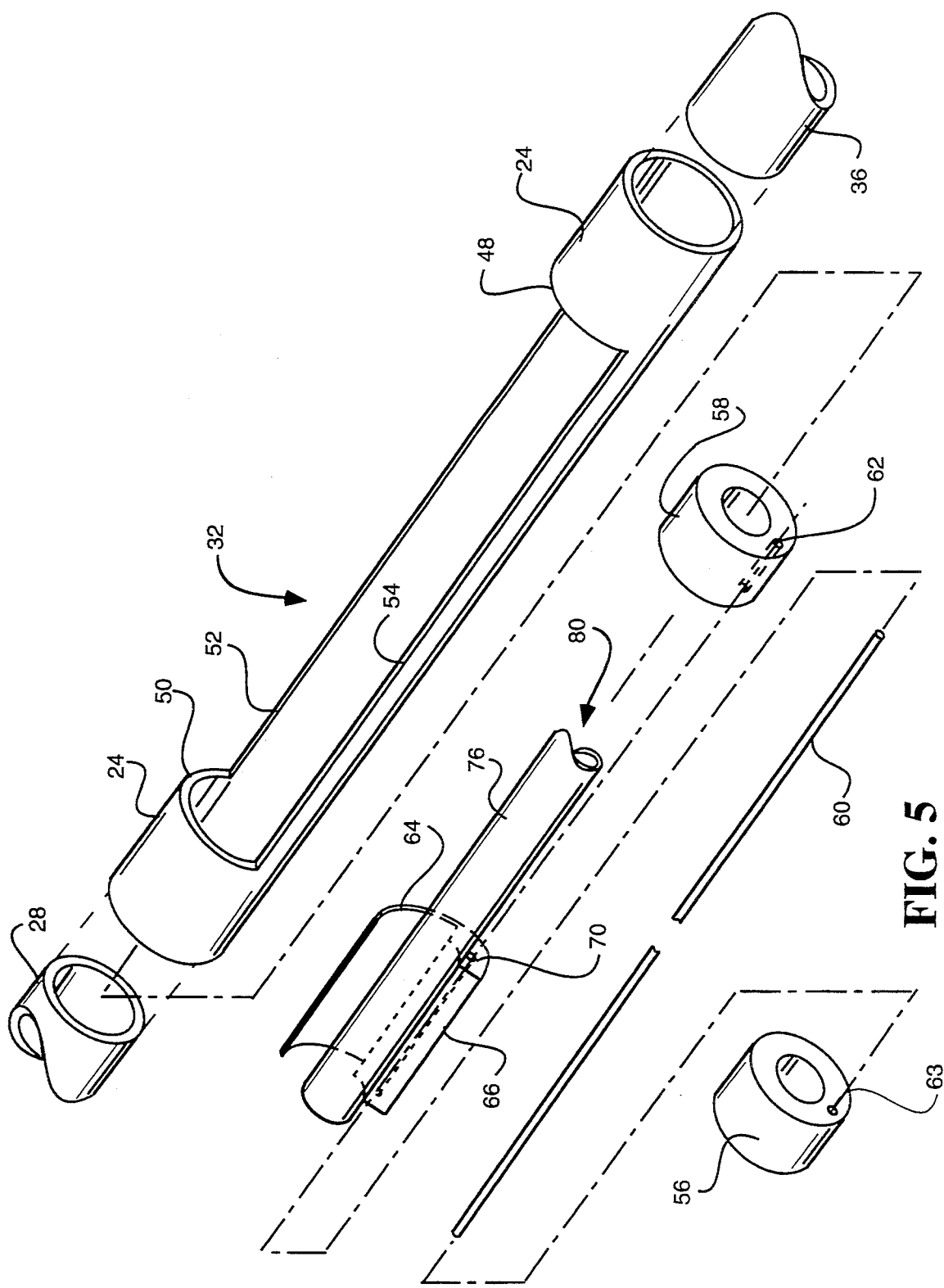
FIG. 5 is an exploded view of the biaxial cutting apparatus of FIG. 2.

With respect to FIGS. 2, 4 and 5 the longitudinal blade edge 68 and edge 54 have a scissors-like cutting action as blade edge 68 is moved reciprocally and rotationally past edge 54 by drive unit 46. As shown the edge 54 is spiral. However, and as will be appreciated by those skilled in the art, the edge 54 may well be straight to be effective. Thus, a straight edge is also within the scope of this invention.

As shown, the blade edge 68 intersects the spiral edge 54 at a single cutting point as the blade 64 is translated longitudinally. The intersection point of blade edge 68 and spiral edge 54 moves along the blade edges as the blade 64 is rotated in a direction determined by the spiral angle of the edge 54 relative to the housing 24 axis. The longitudinal edge 54 is configured to provide a parting edge for separating the tissue slice cut by blade edge 68 from the stenotic tissue invaginated into the housing window 32.

FIGS. 9 and 10 indicate exaggerated views of the configuration of the parting edge 54. The edge 54 is formed as a segment of a shallow spiral lying in the circumference of the cylindrical outer housing 24. This segment edge 54 connects the distal window edge 50 and proximal window edge 48.

The angle of the spiral edge 54 relative to the axis of the housing 24 and the rotational speed of the drive unit 46 relative to the axial reciprocation frequency are selected to cause the successive reciprocations of blade edge 68 to cut and separate suitably small longitudinal increments of the tissue slice from the stenotic tissue remaining in the biological conduit.

The opening of the window 32 with the spiral edge 54 is determined by the angular difference of the sectors of the housing 24 defined by distal window edge 50 and proximal window edge 48 relative to the window edge 52. The preferred angular difference of the sectors is 10° for a spacing between the distal edge 50 and proximal edge 48 of about 0.4 inches.

The shallow spiral edge 54 provides a cutting surface against which the blade edge 68 finally separates the tissue slice from the stenosis. The separation occurs in a series of axial cuts as the blade edge 68 is rotatably advanced from the nearest end of the spiral edge 54 beyond the farthest end of the spiral edge 54.

At the point at which the blade edge 68 passes the farthest end of the spiral edge 54, the tissue slice is fully separated from the stenosis. The separated tissue slice is thus contained and covered by blade 64. The rotation of the blade 64 may be stopped at this point or continued further as desired by the clinician.

The base 66 is provided with a slidable bore hole 70 for receiving guide beam 60 therethrough. The bore hole 70 is disposed longitudinally in the base 66. The bore hole 70 is adapted to fit closely around beam 60. The base 66 and the blade 64 are slidably disposed in an axial direction on the guide beam 60.

The proximal end of the beam 60 is mounted in the hole 63 at the distal surface of the bearing 58 with epoxy. The bearings 56 and 58 attached by the guide beam 60 provide a freely rotatable but longitudinally stable structure for guiding the cutter blade 64. The guide beam 60 is made of a stiff material such as stainless steel. The diameter of the guide beam is typically more than 0.005 inches and less than 0.020 inches.

The arcuate cutter blade 64 is fixedly mounted to the base 66. The blade 64 is slidably disposed inside the housing 24 between the bearings 56 and 58.

The blade edge 68 is essentially coincident with the inner circumference of housing 24. The blade edge 68 is oriented essentially parallel to the axis of housing 24. The blade edge 68 defines a circular cutting plane just inside the inner circumference of the housing 24.

The blade edge 68 has a proximal corner 72 and distal corner 74. The length of the blade 68 from corner 72 to corner 74 is typically 0.1 inches. The blade corner 72 passes the distal window edge 50 on the extreme distal stroke of the blade 64. The blade corner 74 passes the proximal window edge 48 on the extreme proximal stroke of the blade 64.

The combined structure of the bearings 56, 58, the guide beam 60, and the blade 64 are free to rotate within the housing 24. The bearings 56 and 58 holding the beam 60 are constrained longitudinally by the proximal end of nose cone 28 and the distal end of catheter assembly 36. The blade 64 and the beam 60 rotate together with the bearings 56 and 58. The blade 64 is constrained to the longitudinal space defined by the respective proximal end of the bearing 56 and the distal end of bearing 58.

An elongate tubular drive shaft 76 having a distal and a proximal end is disposed in the catheter 36. The drive shaft 76 is made from a suitably strong and flexible material, preferably a nickel-titanium alloy. The diameter of tubular drive shaft 76 is typically 0.020 to 0.040 inches. The outer surface of the distal end of shaft 76 is mounted fixedly by adhesive means such as epoxy to a concave mounting surface 78 provided on the blade mounting base 66. The proximal end of the shaft 76 is connected to the drive unit 46.

The outer circumference of the distal end of the drive shaft 76 and the mounting surface 78 are configured to be coaxial with the axis of housing 24. The bearing 58 has a coaxial hole 82 provided therethrough. The drive shaft 76 passes slidably and rotatably through the hole 82 in the distal bearing 58.

The hole 82 in bearing 58 is coaxial with the center of the housing 24. The drive shaft 76 continues proximally therefrom through the flexible catheter assembly 36 and the proximal assembly 38 to connect at the proximal end of shaft 76 to the biaxial control unit 46. The drive shaft 76 is provided with a lumen 80 therethrough for passage of instruments such as a guide wire (not shown) or fluids.

An annular chamber 84 is defined by the interior of the housing 24 not occupied by the base 66, the shaft 76 and the blade 64. The chamber 84 provides a receptacle to receive tissue as it is cut by blade 64 from the invaginated stenosis within the housing 24.

The chamber 84 allows the accumulation of cut tissue within the housing 24 to proceed without causing the cut tissue to back up or otherwise provide resistance for further ingression of tissue as the blade 64 is rotated.

The drive unit 46 contains a drive mechanism (not shown) connected to a clockworks (not shown) for reciprocating the connection 44 in alternate proximal and distal strokes. Additionally the drive mechanism and clockworks rotate the connection 44. The connection 44 is mounted to the proximal end of drive shaft 76. Reciprocation and rotation of the connection 44 is transmitted from the clockworks to the drive shaft 76 by the connection 44 relative to the flexible catheter 36 and housing 24.

The ratio of axial reciprocation to rotation of the clockworks is arranged so that one distal and proximal stroke of the drive shaft 76 will be accompanied by a suitably small angular motion of the drive shaft. A typical ratio of reciprocation to rotation is 2000 axial cycles for each complete rotation of the drive shaft 76.

The clockworks is configured such that the each distal stroke of the connection 44 will be communicated by the drive shaft 76 to cause the distal corner 74 of blade edge 68 to pass the distal window edge 50. Each proximal stroke of the connection 44 will similarly cause the proximal corner 72 of blade edge 68 to pass the proximal window edge 48. The clockworks is further configured such that the advance of blade edge 68 from a covered position within housing 24 will begin from the window 32 first longitudinal edge 52 towards the window 32 opposite longitudinal edge 54, i.e. in the direction of cutting of the invaginated tissue.

Such a clock works can be easily constructed by one skilled in the mechanical arts. Once the length of the blade 64, the length of window 32 and the desired angular displacement of blade edge 68 per reciprocation cycle has been chosen, the clock works included in drive unit 46 can be specifically designed and constructed to provide the desired motion.

TYPICAL OPERATION

With respect to FIG. 1, the use and operation of the apparatus to surgically remove a stenosis in the blood vessel of a patient is described below. The cutting apparatus 26 is positioned in the catheter housing 24 such that the blade 64 is covered by the housing 24 and in a position to begin cutting adjacent to window edge 52.

An opening is prepared in a suitable vessel as, for example, the femoral artery, and the catheter 20 is guided by means of the guide wire 30 to a desired location in the vasculature while being observed, for example by fluoroscopic means (not shown). The housing 24 is then rotationally and longitudinally positioned by manipulation of catheter 38 until the window 32 is adjacent to the stenosis, the balloon 34 is then inflated, urging the window 32 toward the stenosis, thereby allowing invagination of the tissue to be cut.

The drive unit 38 is started and the clock works begins to move the blade 84 in alternate distal and proximal strokes as the blade edge 88 slowly rotates toward the invaginated tissue between initial edge 52 and parting edge 54. Successive cuts will be made in the invaginated tissue as the blade proceeds across the open window 32. A wide slice of tissue with length determined by the length of window 32 and depth determined by the amount of invagination will be directed into the housing 24 and chamber 84.

As the blade 84 is exerting cutting force on a very small cross section of tissue with each forward and backward pass, the tissue in front of the blade edge 88 will tend to remain relatively undistorted. This results in a wider, more uniform cut and tends to reduce the teardrop and scallop effect noted with cutters which direct the cutting force primarily perpendicular to the blade edge.

The rotation of blade 84 continues as blade edge 88 approaches the parting edge 54. At each reciprocal distal and proximal stroke of blade 68, the drive unit 48 advances the blade 88 edge rotationally beyond an increment of the opposite spiral part-off window edge 54. This scissors-like action causes an increment of the slice of tissue to be parted from the stenosis remaining outside the housing 24. The incremental separation minimizes the distortion of the tissue edge since the cutting force is applied to only a small segment at each point.

Successive strokes and cuts continue until the slice is completely separated from the stenosis and captured by the chamber 84. The shape of the tissue remaining outside the housing at the separation edge has a well defined geometry with a satisfactorily shallow incline. The balloon 34 is deflated. At this point the housing 24 can be repositioned by the catheter 36 for further cuts, or can be removed from the vasculature to dispose of the tissue entrapped in housing 24.

A PREFERED EMBODIMENT

An alternate embodiment of a biaxial cutting apparatus in accordance with this invention is described below.

In general, a means for controlling the depth of invagination of tissue into housing 24 is added to the biaxial cutter in accordance with this invention. This is illustrated by the track cutter assembly 100 in FIGS. 6-8.

The track cutter assembly 100 has a tubular housing 24 having an axis and a distal and proximal end disposed on the distal end of a flexible catheter 36 as shown in FIG. 1. The housing 24 has a cutout window 32. The window 32 is defined by distal edge 50, proximal edge 48, first longitudinal edge 52 and second longitudinal parting edge 54. The parting edge 54 is configured as a segment of a shallow spiral as described above.

The width of the window 32 opening between the longitudinal edges 52 and 54 is defined by an angle e typically between 100° and 270° with respect to the axis of housing 24.

A cylindrical axial cutter guide assembly 102 is provided to fit slidably and rotatably within housing 24. Cutter axial guide 102 is made of a suitably rigid tubular material such as stainless steel and has an outer diameter which fits closely and rotatably within the inner diameter of housing 24. The outer surface of the cutter axial guide 102 is provided with a circumferential bearing surface between housing 24 and guide 102. The length of axial guide 102 is shorter than the length of housing 24. The distal and proximal ends of guide 102 are provided with smooth surfaces suitable for sliding on bearing surfaces.

The axial cutter guide assembly 102 is further provided with an inner window 104. The inner window 104 is defined by the circular distal and proximal edges 106 and 108 and the first longitudinal edge 110 and the ingress edge 112. The length of the inner window 104 from the edge distal 106 to the proximal edge 108 is greater than or equal to the length of the outer window 32 from distal edge 50 to proximal edge 48 of housing 24. The width of the inner window opening 104 from the blade edge 68 to the ingress edge 112 is defined by an angle $\Phi$ less than or equal to the angle $\theta$ defining the invagination extent of window opening 32. A typical angle $\Phi$ for the inner window 104 is 20 degrees with respect to the axis of housing 24.

The spacing from the blade edge 68 to the inner window ingress edge 112 controls the depth of tissue invaginated into the housing 24 when the guide 102 is rotated into position for cutting.

The angular position of the guide 102 can be changed by the drive unit 46 and the drive shaft 76. There are three important angular positions. First, an initial position having the window 100 closed wherein the cutting blade 64 is shielded from the blood vessel. Second, a cutting position with the cutting blade in contact with tissue. Third, another closed position after cutting with the cut tissue entrapped within the guide 102.

The cutter axial guide 102 is located longitudinally within the housing 24 such that the distal inner window circular edge 106 lies coincident with or distal to the circular distal edge 50 of the housing 24. The proximal circular inner window edge 108 lies coincident with or proximal to the proximal circular edge 48 of the housing 24.

The axial guide 102 is fixed distally within the housing 24 by a smooth bearing surface provided on the proximal end of the nose cone 28. The distal bearing surface of the nose cone 28 abuts slidably against the distal end of the guide 102.

The axial guide 102 is fixed proximally within the housing 24 by a smooth bearing surface provided on the distal end of catheter 36. The distal bearing surface of the catheter 36 abuts slidably on a the bearing surface 150 on the proximal end of guide 102.

The proximal end of nose cone 28 is configured to mount closely into the distal end of housing 24 and is fixed in place by suitable means such as adhesive into a slidable, abutting relationship with the distal end of cutter axial guide 102.

The distal end of flexible catheter 36 is configured to mount closely into the proximal end of housing 24 and is also fixed in place by suitable means into a slidable, abutting relationship with the proximal end of cutter axial guide 102.

The track cutter assembly 100 is thus provided with an inner window 104 rotatably movable with respect to the housing 24 outer window 32. This inner window 104 provides a means for controlling the degree of invagination for tissue entering the housing 24. By selecting a configuration with the angle $\Phi$ of the window 104 between the blade edge 68 and the guide 102 ingress edge 112, the invagination of tissue into the housing 24 can be selected to be any desired value from some minimum, as little as zero with no opening, to some maximum determined by the width of the housing 24 outer window 32. The depth of tissue invagination will tend to remain constant as the inner window 104 is rotated into and across the outer window 32. The blade edge 68 will therefore be presented with a generally uniform thickness to be cut. This provides a degree of thickness control unavailable by previous art in atherectomy. Tests have shown a very low variation of depth of cut relative to the average depth of cut. The lower variance of cutting depth of the biaxial cutting apparatus of this invention thus provides the clinician with a greater margin of safety to avoid perforation of the blood vessel wall when cutting stenoses.

The inner window 104 provides a controllable depth of tissue invagination to be presented to a cutting blade 64 slidably disposed in the cutter guide 102 and will now be described below with reference to FIG. 6 and 7.

The cutter guide 102 contains an integral thickened support region 114 running the full longitudinal length of guide 102. The region 114 projects generally inward from a point near the cutter guide edge 110 and curls counter-clockwise around the interior of guide 102 to form a longitudinal, generally tubular enclosed C-shaped track 116 having a narrow slot 118 therethrough.

The narrow slot 118 is defined by two rounded edges 120 and 122 of the track 116. The first track edge 120 is adjacent to cutter guide edge 110. The second track edge 122 is located such that the slot 118 is facing upward toward the inner window opening 104.

The tubular track 116 is typically 0.025 inches in width. The guide 102 has an outer track wall 124 defining a cover. Cover 124 is extended from the track 116 in a circular direction away from the cutting direction of the blade edge 68. The cover 124 extends angularly between the track guide edge 110 and the ingress edge 112

The cover 124 is sized to provide a closure to window 32 when the guide 102 is rotated such that the track guide edge 110 and the ingress edge 112 are adjacent to the housing 24 parting edge 54 and the edge 52 respectively.

The diameter of the housing 24 is typically 1.5 to 4.0 mm. The track 116 is located on an axis offset but parallel relative to the central axis of the housing 24.

The C-shaped track 116 has an inner wall 126 facing radially inward toward the guide 102. The track inner wall 126 and the opposite inner wall 128 of the guide 102 form a chamber 130 for receiving cut tissue or for passage of other instruments or materials. The track 116 has an axis offset by a preselected radial distance from the axis of the housing 24. The track 116 axis offset allows for a larger volume for chamber 130 for such passage than a guide track located in the center of the housing 24 as described in the first embodiment.

A blade mounting member 132 is configured to fit closely and slidably into the track 116. An integral projection 134 from member 132 protrudes upward through slot 118. The shape of projection 134 is configured fit precisely between the opposed rounded edges 120 and 122.

The projection 134 connects mounting member 132 to a cutting blade 64 having a convex arcuate outer surface 136 and a blade edge 68. The blade surface 136 extends from blade edge 68 to the track edge 110. The blade edge 68 is essentially parallel to the first longitudinal inner window edge 110, the second longitudinal inner window ingress edge 112, the first longitudinal outer window edge 52. The second longitudinal window edge 54 forms a part-off cutting edge. The outer arcuate surface 136 and blade edge 68 lie next to the inner circumference of the housing 24 and thereby define a circular cutting plane contiguous therewith.

The track 116 and slot 118 of cutter guide 102 form an axial guide means for supporting and guiding the blade mounting member 132 and the blade 64 in a longitudinal cutting path parallel to the axis of the outer housing 24, when the guide 102 is in a fixed angular position within the housing 24.

Cutting blade edge 68 is terminated at the proximal end of blade 64 by corner 72 and at the distal end of blade 64 by corner 74. The longitudinal length of the cutting blade 68 is typically 0.1 inch.

The blade 64 has an concave arcuate interior surface 138 which is curved to direct cut tissue smoothly from the blade edge 68 into the interior chamber 130.

Mounting member 132 is provided with a longitudinal hole 140 therethrough coaxial to the track 116 for receiving the distal end of the drive shaft 76. The distal end of the drive shaft 76 is fixedly mounted by suitable means such as solder or adhesive inside the mounting hole 140.

The drive shaft 76 passes proximally through the catheter 36, infusion assembly 38 to the connection 44 and drive unit 46.

Figure 8:
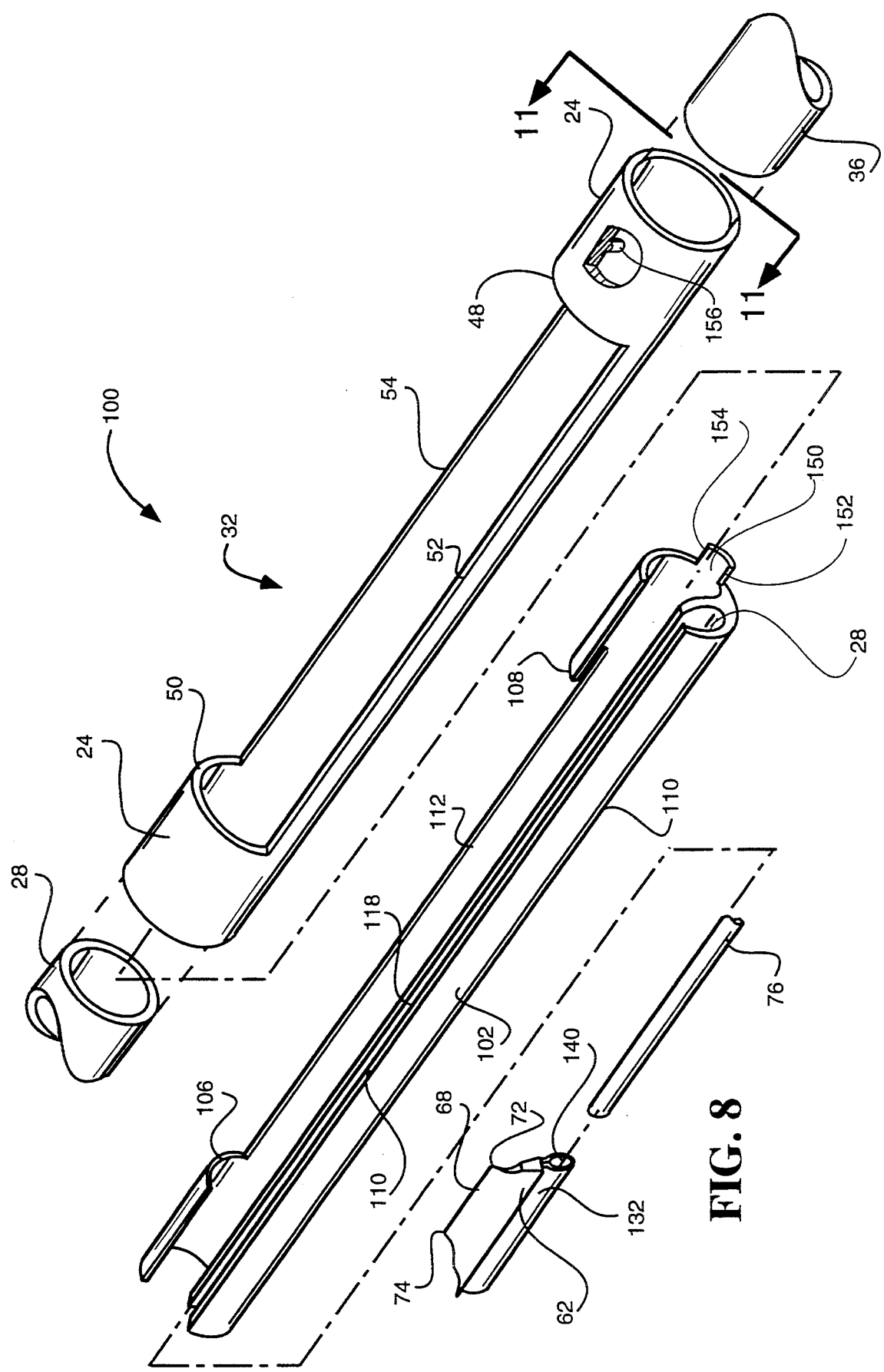
FIG. 8 is a exploded view of the preferred embodiment of FIG. 6 illustrating a rotational stop.

With respect to FIG. 8 a cutout depicting a portion of the interior of the proximal end of outer housing 24 is illustrated. A rotational stop post 156 projects radially inward from the inner circumference of the proximal end of the housing 24. The post 156 is fixedly mounted to the housing 24. The post 156 projects sufficiently inward therefrom to prevent the outer circumference of inner guide 102 from passing thereby. A longitudinal sector 150 is defined by a first rotational stop edge 152 and a second rotational stop edge 154 and the guide 102 proximal bearing edge. the edge 152 and the edge 154 project longitudinally inward from the proximal end of guide 102 and form the longitudinal boundaries of the proximal sector 150.

The proximal end of guide 102 between the edges 152 and 154 forming the sector 150 is located proximally to the stop post 156.

The stop edge 152 of the sector 150 is configured relative to the angular position of the blade edge 68. The first stop edge 152 of the sector 150 will contact one side of the housing post 156 in a first position. The first stop position provides a holding position for the blade edge 68 prior to the blade edge 68 passing the initial outer window edge 52.

The stop edge 154 of the sector 150 is configured relative to the angular position of the blade edge 68. The edge 154 will contact the opposite side of the housing post 156 in a second position. The second stop position provides a holding position for the blade edge 68 after passing the parting edge 54.

The first stop position allows the clinician to preset the blade 68 firmly in a known starting position relative to the outer window and opposite to the direction of cutting before exposing the blade to the biological conduit for cutting.

The second stop position allows the clinician to complete the tissue cutting with the blade edge 68 in a known finish position past the outer window with the blade edge 68 unexposed to the conduit and with the cover 124 of the guide 102 over the window 32.

It is an advantage provided by this invention for the clinician to have known starting and finish positions for the blade edge 68 firmly defined relative to the catheter housing window 32.

Operation of the improved embodiment is similar to that described above in the first embodiment. The advantages of the addition of the rotatable narrow inner window 104 relative to the larger, fixed outer window 32 to limit and control tissue invagination and thereby the depth of cut have been described above. It is also an advantage provided by this invention, to reduce the variation in the depth of cut as described above.

While the foregoing detailed description has described several embodiments of the biaxial cutter in accordance with this invention, it is to be understood that the above description is illustrative only and not limiting of the disclosed invention. It will be appreciated that it would be possible by one skilled in the art to modify a number of things for example, the size of the windows, the shape and number of blade edges, the shape and location of the guide track, the thicknesses of and the materials used. Using the principles disclosed in accordance with this invention one can include or exclude various elements within the scope and spirit of this invention. Thus the invention is to be limited only by the claims as set forth below.

What is claimed is:

1. A cutter apparatus for use with a catheter within a biological conduit, comprising:
a tubular member defining a housing, the housing having a window for intimate contact with tissue in the biological conduit, the window including a distal edge and a proximal edge and having an edge between the distal and proximal edges having at least one contiguous submultiple edge defining a parting edge, each submultiple edge including at least one spiral increment; and
a cutter assembly including:
cutting means for cutting tissue within the biological conduit,
means for rotating the cutting means within the housing, and
means for translating the cutting means within the housing,
whereby the cutting means is adapted to remove a slice of tissue from within the biological conduit by rotating and translating the cutting means.

2. The cutter apparatus as set forth in claim 1, wherein there is a plurality of submultiple edges each having at least one spiral cutting increment, the spiral cutting increments defining a continuous line along each respective submultiple edge.

3. The cutter apparatus as set forth in claim 2, wherein the housing includes an inner circumference and wherein the cutting means includes a slidable and rotatable blade cutting edge lying adjacent to a surface defined by the inner circumference of the housing.

4. The cutter apparatus as set forth in claim 3, wherein the means for rotating the cutting means defines a direction of rotation and the blade edge defines a cutting direction facing in the direction of rotation,
whereby the parting edge and the blade edge cooperate for removing a slice of tissue from the biological conduit tissue by separating the slice from the conduit tissue by rotating and translating the blade edge past the parting edge in the cutting direction.

5. A cutter apparatus for use with a catheter within a biological conduit, comprising:
a tubular member defining a housing, the housing having a window for intimate contact with tissue in the biological conduit; and
a cutter assembly including:
cutting means for cutting tissue within the biological conduit,
means for rotating the cutting means within the housing, including a rotational limit means for limiting the extent of a rotational cutting stroke of the cutting means, the rotation being limited to a preselected portion of one complete rotation, the means for limiting rotation having a first limit defining the beginning of a rotational cutting stroke wherein the cutting means is positioned prior to cutting tissue in contact with the housing window, the means for limiting rotation further having a second limit defining the end of the rotational cutting stroke wherein the cutting means is positioned after completing a cutting stroke past the housing window, and
means for translating the cutting means within the housing,
whereby the cutting means is adapted to remove a slice of tissue from within the biological conduit by rotating and translating the cutting means.

6. A cutter apparatus for use with an atherectomy catheter, comprising:
a tubular member defining an atherectomy catheter outer housing, the outer housing having outer and inner surfaces, the outer housing further having a window for intimate contact with tissue in a biological conduit;
a cutter means within the outer housing, the cutter means including:
means for rotating the cutter means within the outer housing, said means defining a direction of rotation,
means for translating the cutter means within the outer housing, and
blade means for cutting tissue within the biological conduit, the blade means having a slidable and rotatable blade edge for cutting tissue, the blade edge configured to lie immediately adjacent to and in contact with the inner surface of the catheter housing, the blade edge defining a rotational cutting direction essentially perpendicular to the blade edge and facing in the direction of rotation; and
an inner housing rotatably disposed within and immediately adjacent to the inner surface of the outer housing, the inner housing having an inner window means for invagination of conduit tissue through the outer window into the inner housing, the inner window means enclosing the blade edge, the inner window means further having a tissue ingress edge spaced apart from and parallel to the blade edge in the rotational cutting direction, the ingress edge located immediately adjacent to the inner surface of the outer housing, the distance between the blade edge and the spaced apart ingress edge being selected to limit the angular extent of tissue invaginated through the outer housing window into the inner housing between the ingress edge and the blade edge,
whereby the cutting means is adapted to remove a slice of tissue of a controlled thickness from within the biological conduit by rotating and translating the cutting means.

7. The cutter apparatus as set forth in claim 6, wherein the blade means has an arcuate concave interior surface projecting inward from the blade edge toward the interior of the inner housing for directing cut tissue into the inner housing.

8. The cutter apparatus as set forth in claim 6, wherein the distance between the blade edge and the spaced apart ingress edge is selected to limit the angular extent of tissue invaginated into the inner housing between the ingress edge and the blade edge to a value between 0° and about 270°.

9. The cutter apparatus as set forth in claim 6, wherein the distance between the blade edge and the spaced apart ingress edge is selected to limit the angular extent of tissue invaginated into the inner housing between the ingress edge and the blade edge to a value of about 20°.

10. The cutter apparatus as set forth in claim 6, wherein the outer housing window includes:
a distal edge and a proximal edge
a parting edge between the distal edge and proximal edge, the parting edge being comprised of one or more contiguous submultiple edges of the length of the parting edge, each submultiple edge comprising a succession of one or more spiral cutting increments, the succession of spiral cutting increments forming a continuous line along each respective submultiple edge, beginning at one end of each submultiple edge, the spiral cutting increments of each submultiple edge terminating at the opposite end of each submultple edge, the spiral cutting increments of each submultiple edge being smoothly and continuously displaced in a circumferential direction defined by the rotation of the cutter means, each spiral increment of each submultiple edge having a cutting edge lying adjacent to the inner surface of the outer housing; and the cutter means including a blade cutting edge lying immediately adjacent to the inner surface of the outer housing, the blade cutting edge defining a cutting direction facing in the direction of the parting edge and facing in the rotational cutting direction;

whereby the parting edge and the blade cutting edge cooperate for removing the slice of tissue from the biological conduit tissue by separating the slice from the conduit tissue by rotating and translating the blade cutting edge past the parting edge in the rotational cutting direction.

11. The cutter apparatus as set forth in claim 6, wherein the means for rotating the cutter means includes a rotational limit means for limiting the extent of a rotational cutting stroke of the cutter means to a preselected portion of one complete rotation, the means for limiting rotation having a first limit defining the beginning of a rotational cutting stroke wherein the cutter means is positioned prior to cutting tissue in contact with the housing window, the means for limiting rotation further having a second limit defining the end of the rotational cutting stroke wherein the cutter means is positioned after completing a cutting stroke past the housing window.

12. A cutter apparatus as set forth in claim 11, wherein:

the cutter means includes a rotatable cover means for closing the housing window, the cover means being interposed coaxially between a portion of the blade means and immediately adjacent to the inner surface of the outer housing, the cover means mounted in fixed rotatable relation with the blade means, the cover means being sized to entirely close the housing window when the blade means and cover means are rotated into a closed position, whereby the tissue removed from the biological conduit will be entrapped within the housing when the housing window is closed by the cover means.

* * * * *